United States Patent [19]
Weber-Unger

[11] Patent Number: 5,316,147
[45] Date of Patent: May 31, 1994

[54] CASE FOR RECEIVING A BREAST PROSTHESIS

[75] Inventor: Georg Weber-Unger, Kufstein, Austria

[73] Assignee: Dr. Helbig GmbH & Co Orthopädische Produkte KG, Brannenburg, Fed. Rep. of Germany

[21] Appl. No.: 116,069

[22] Filed: Sep. 1, 1993

[30] Foreign Application Priority Data

Sep. 11, 1992 [DE] Fed. Rep. of Germany ....... 9212261

[51] Int. Cl.⁵ .............................................. B65D 81/06
[52] U.S. Cl. ..................................... 206/438; 206/592
[58] Field of Search ............... 206/438, 521, 523, 587, 206/591-594; 623/7, 8

[56] References Cited

U.S. PATENT DOCUMENTS

| | | | |
|---|---|---|---|
| 3,755,042 | 8/1973 | Robertson et al. | 206/438 |
| 4,697,703 | 10/1987 | Will | 206/438 |
| 4,750,619 | 6/1988 | Cohen | 206/438 |
| 4,881,562 | 11/1989 | Wright et al. | 206/523 |
| 4,934,534 | 6/1990 | Wagner | 206/523 |
| 5,037,436 | 8/1991 | Heaston | 206/438 |
| 5,148,920 | 9/1992 | Walker | 206/438 |
| 5,193,679 | 3/1993 | White | 206/438 |
| 5,236,088 | 8/1993 | Dhority et al. | 206/523 |

Primary Examiner—Jimmy G. Foster
Attorney, Agent, or Firm—Feiereisen & Kueffner

[57] ABSTRACT

A case for receiving a breast prosthesis includes a main body and a cover for closing the main body, with the main body being filled with elastic material such as to include a depression which opens toward the cover. The depression is funnel-shaped in unstressed state i.e. when the case is empty, and essentially conforms to the configuration of a breast prosthesis when the latter is placed in the case.

12 Claims, 1 Drawing Sheet

1

CASE FOR RECEIVING A BREAST PROSTHESIS

BACKGROUND OF THE INVENTION

The invention refers to a case for receiving a breast prosthesis, and in particular to a case of the type having a main body which is closable by a cover and is filled with elastic material in a manner to include a depression which opens towards the cover.

A case of this type is commercially available and includes a square carrier bag of plastic material which contains a foamed body. Provided in the foamed body is a concave recess for receiving in form-fitting manner a breast prosthesis so that the tip of the prosthesis points to the bottom of the case. A part of the top of the carrier bag constitutes a cover with two zippers for opening and closing and prevents the prosthesis placed in the concave recess from falling out of the recess. A carrying strap by which both zippers are connected allows a simultaneous use of the zippers and serves as a handle.

A case of this type has the drawback that the foamed body of the carrier bag is molded as a negative to precisely conform to the configuration and size of a particular breast prosthesis. Thus, when using this case for a different configuration and/or size of a breast prosthesis, a different foamed body with the negative configuration of such breast prosthesis must be inserted in the case. Consequently, this prior art case requires a particular foam body for each configuration and size of a breast prosthesis. This requirement not only increases manufacturing costs for the case but also increases the storage costs since for each shape and size of a breast prosthesis, a respective case with a carrier bag and a foamed body must be made available. The user must therefore acquire a separate prosthesis case or at least a separate foamed body when changing the prosthesis shape and/or size for placement therein.

SUMMARY OF THE INVENTION

It is an object of the present invention to provide an improved breast prosthesis case obviating the aforestated drawbacks.

In particular, it is an object of the present invention to provide an improved breast prosthesis case which is adaptable for use with varying shapes and/or sizes of breast prostheses.

These objects, and others which will become apparent hereinafter, are attained in accordance with the present invention by filling the main body of the case with an elastic material in such a manner as to include a depression which is generally funnel-shaped and essentially adapts to the configuration of a breast prosthesis when the latter is placed in the main body.

Preferably, the elastic material is a fiber material, such as textile fibers, preferably monofilaments, available in commerce under the name of "Fiberfill". This fiber material is sufficiently soft to adapt to varying prosthesis shapes and/or sizes and is of a suitable strength to sufficiently support the relatively heavy prosthesis within the case. Alternatively, the elastic material may also contain a foam material, such as flakes of polyurethane, for use as filler for the main body.

The configuration of a depression with a tip which is suitably connected to the bottom of the main body is advantageous as the position of the depression relative to the case is fixed.

Suitably, the depression may be covered by a fine-meshed fabric which displays a visually pleasing appearance and contains the fiber material in a closed space between the fabric and the main body. Preferably, the fine-meshed fabric is a textile fabric which is characterized by a certain stretching ability, such as spandex which is an elastic synthetic fiber, usually of polyurethane. The cover of the case may be provided with a padded convex fabric, such as textile fibers, preferably monofilaments or flaky foam material of polyurethane which is in contact with the depression and bears against the breast prosthesis placed in this depression during closing of the cover so as to provide further support of the prosthesis.

BRIEF DESCRIPTION OF THE DRAWING

The above and other objects, features and advantages of the present invention will now be described in more detail with reference to the accompanying drawing in which sole

DETAILED DESCRIPTION OF PREFERRED EMBODIMENTS

Figure 1:
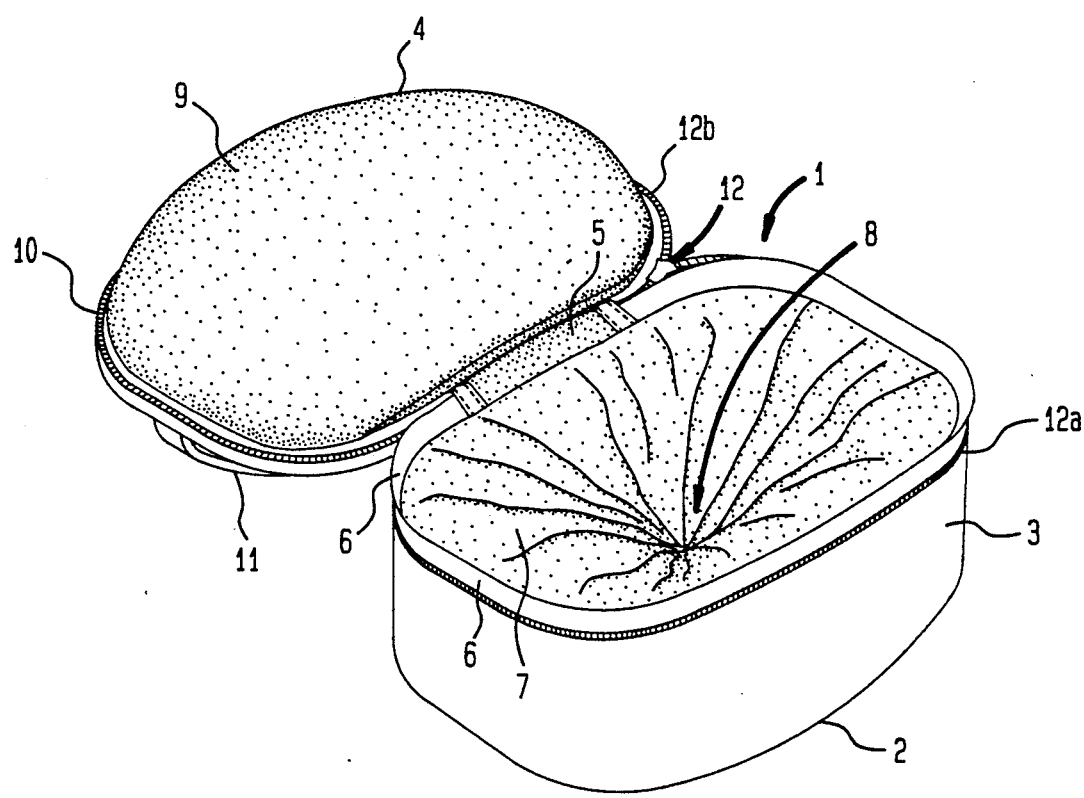
FIG. 1 shows a perspective illustration of one embodiment of a case for receiving a breast prosthesis in accordance with the present invention.

FIG. 1 shows a perspective view of one embodiment of a case for receiving a breast prosthesis, generally designated by reference numeral 1 and including an open main body 2, 3 which is closable by a cover 4. The main body includes an oval-shaped bottom 2 and a circumferential side wall 3 which extends upwards from the bottom 2. The cover 4 is linked by a connecting element 5 to a section of the top edge 6 of the side wall 3, with a zipper, generally designated by reference numeral 12, being provided to close the case with the cover 4. The zipper 12 extends from one side of the connecting element 5 to the other side thereof, with one zipper tape 12a extending about the circumference of the case 1 in proximity of the top edge 6 and with the other zipper tape 12b extending about the circumference of the cover 4. A fabric 7 is attached along the circumference of the top edge 6 to the side wall 3 and formed in such a manner that a funnel-shaped depression 8 is created, with the tip of the depression 8 being fixed to the oval-shaped bottom 2, e.g. by a seam, so that a space is provided beneath the fabric 7 which is defined by the fabric 7, side wall 3 and bottom 2.

The fabric 7 is preferably a fine-meshed textile fabric which is characterized by a certain stretching ability. A suitable material is spandex which is an elastic synthetic fiber, usually of polyurethane.

The cover 4 is also provided with a fabric 9 which is of similar material as fabric 7 and is attached to the cover 4 along the perimeter 10 thereof to create a space between the fabric 9 and the cover 4.

Suitably, the spaces beneath the fabrics 7, 9 are filled with elastic material, such as textile fibers, preferably monofilaments, available in commerce under the name of "Fiberfill". This fiber material is sufficiently soft to adapt to varying prosthesis shapes and/or sizes and is of a suitable strength to sufficiently support the relatively heavy prosthesis within the case. Alternatively, the elastic material may also contain a foam material, such as flakes of polyurethane, for use as filler for the main body.

The fabric 7 of elastic fiber material is incorporated in the main body 2, 3 of the case 1 such that a funnel-shaped depression 8 is created when the case 1 is empty while conforming to the shape of a breast prosthesis when the latter is placed in the case 1. The elastic fiber material in the cover 4 is arched so that the inside surface of the fine-meshed fabric 9 of the cover 4 is of convex configuration.

Suitably, the exterior of the cover 4 is provided with a handle 11 which extends across the case 1.

When using the case 1 for transporting or protecting a breast prosthesis, the latter is placed in the funnel-shaped depression 8 within the case 1 in such a manner that the tip of the prosthesis points towards the bottom 2 of the case 1. The funnel-shaped depression 8 adapts to the shape of the prosthesis as the elastic fiber material gives way and conforms to the prosthesis being placed in the case. By closing the case 1 with the padded cover 4, the prosthesis is retained between the fabrics 7, 9 through the elastic fiber material so that the prosthesis can be softly stored within the case 1.

While the invention has been illustrated and described as embodied in a case for receiving a breast prosthesis, it is not intended to be limited to the details shown since various modifications and structural changes may be made without departing in any way from the spirit of the present invention.

What is claimed as new and desired to be protected by Letters Patent is set forth in the appended claims:

1. A case for receiving a breast prosthesis, comprising:
    a main body and;
    a cover for closing said main body, said main body being filled with elastic material such as to include a depression which opens toward said cover, said depression being funnel-shaped when being unstressed and essentially conforming to the configuration of a breast prosthesis when the latter is placed in said main body.

2. A case as defined in claim 1 wherein the elastic material is a fiber material.

3. A case as defined in claim 1 wherein the elastic material is provided in form of flakes of foamed material.

4. A case as defined in claim 1 wherein said depression defines a tip which reaches towards said bottom of said main body.

5. A case as defined in claim 1 wherein said depression is covered by a fine-meshed fabric.

6. A case as defined in claim 5 wherein said fine-meshed fabric has a tip connected with said bottom of said main body.

7. A case as defined in claim 1 wherein said cover has a convex inside surface.

8. A case as defined in claim 7 wherein said cover is provided with a fine-meshed fabric to define said convex inside surface.

9. A case as defined in claim 8 wherein said cover is filled with fiber material.

10. A case as defined in claim 5 wherein said fine-meshed fabric is elastic.

11. A case as defined in claim 8 wherein said fine-meshed fabric is elastic.

12. A case as defined in claim 1, and further comprising a handle attached to said cover of said case.

* * * * *